United States Patent
Knittel et al.

(10) Patent No.: US 6,649,812 B1
(45) Date of Patent: Nov. 18, 2003

(54) METHOD OF PRODUCTION OF TRANSGENIC PLANTS, WHOLLY PERFORMED IN THE $T_O$ GENERATION, FROM MERISTEMS

(75) Inventors: Nathalie Knittel, Vic (AU); Philippe Lenee, Beaumont (FR)

(73) Assignee: Biogemma, Paris (FR)

( * ) Notice: Subject to any disclaimer, the term of this patent is extended or adjusted under 35 U.S.C. 154(b) by 0 days.

(21) Appl. No.: 09/276,163

(22) Filed: Mar. 25, 1999

Related U.S. Application Data

(63) Continuation of application No. 08/601,004, filed as application No. PCT/FR94/01017 on Aug. 19, 1994, now abandoned.

(30) Foreign Application Priority Data

Aug. 30, 1993 (FR) .............................................. 93 10368

(51) Int. Cl.$^7$ .......................... A01H 1/00; C12N 15/82; C12N 15/87

(52) U.S. Cl. ...................... 800/278; 800/288; 800/293; 800/294

(58) Field of Search ................................. 800/298, 278, 800/279, 281, 293, 294; 435/468, 469, 470

(56) References Cited

U.S. PATENT DOCUMENTS 5,164,310 A    11/1992   Smith et al. ................. 800/294

FOREIGN PATENT DOCUMENTS

| EP | 0 301 749 | 2/1989 |
| EP | 0 400 553 | 12/1990 |
| EP | 0 424 047 | 4/1991 |
| EP | 486233 | 5/1992 |
| EP | 486234 | 5/1992 |
| GB | 2211204 | 6/1989 |
| WO | WO 89/12102 | 12/1989 |
| WO | WO 92/15675 | 9/1992 |

OTHER PUBLICATIONS

Reinert; Aspects of Organization– Organogenesis and Embryogenesis, 1973, Botanical Monographs; Plant tissue and Cell Culture: 338–342.*

McCabe, et al., "Transformation of elite cotton cultivars via particle bombardment", *Biotechnology*, vol. 11, No. 5, May 1993, New York, USA, pp. 596–598.

Christou, et al., "Inheritance and expression of foreign genes in transgenic soybean plants", *Proceedings of The National Academy of Sciences of USA*, vol. 86, Oct. 1989, Washington, USA, pp. 7500–7504.

Christou, et al., "Soybean genetic engineering—commercial production of transgenic plants", *TIBTEC*, vol. 8, No. 6, Jun. 1990, pp. 145–151.

McCabe, et al., "Stable genetic transformationof soybeam (Glycine max) by particle acceleration", *Biotechnology*, vol. 6, No. 8, Augusst 1988, New York, USA, pp. 923–926.

Bidney, et al., "Microprojectile bombardment of plant tissues increases transformation frequency by Agrobacterium", *Plant Molecular Biology*, vol. 18, 1992, The Netherlands, pp. 301–313.

SE Stachel et al (1985) Nature 318: 624–629.

P. Christou, "Morphological Description of Transgenic Soybean Chimeras Created by the Delivery, Integration and Expression of Foreign DNA Using Electric Discharge Particle Acceleration", *Annals of Botany*, 66: 379–386, 1990.

YS Chyi et al (1987) Plant Cell Reports 6: 105–108.

Russell, et al., "Stable transformation of Phaseolus vulgaris via electric–discharge mediated particle acceleration", *Plant Cell Reports*, vol. 12, No. 3, Jan. 1993, pp. 165–169.

Schrammeijer, et al., "Meristem transformation of sunflower via Agrobacterium", *Plant Cell Reports*, vol. 9, 1990, pp. 55–60.

D.L. Bidney, et al.; "Transformed progeny can be recovered from chimeric plants regenerated from Agrobacterium tumefaciens treated embryonic aces of sunflower"; *Proceeding of the 13th International Sunflower Conference*; Sep. 1992; vol. II, pp. 1408–1412.

Paul Christou, et al.; "Prediction of germ–line transformation events in chimeric $R_o$ transgenic soybean plantlets using tissue–specific expression patterns"; *Plant Journal*; 1992; pp. 283–290.

Rhonda L. Gambley, et al.; "Microprojectile transformation of sugarcane meristems and regneration of shoots expressing β–Glucuronidase"; *Plant Cell Reports*; 1993; pp. 353–346.

Toshio Murashige, et al.; "Revised Medium for Rapid Growth and Bio Assays with Tobacco Tissue Cultures"; *Physiologia Plantarum*; 1962; vol. 15, pp. 473–497.

John J. Finer, et al.; "Development of the particle inflow gun for DNA delivery to plant cells"; *Plant Cell Reports*; 1992; pp. 323–328.

L. Herrera–Estrella, et al.; "Chimeric genes as dominant selectable markers in plant cells"; *EMBO Journal*; 1983; pp. 987–995.

A. Depicker, et al.; "Nopaline Synthase: Transcript Mapping and DNA Sequence"; *Journal of Molecular and Applied Genetics*; 1982; pp. 561–573.

(List continued on next page.)

Primary Examiner—Deborah Crouch
Assistant Examiner—Joseph Woitach
(74) Attorney, Agent, or Firm—Merchant & Gould P.C.

(57) ABSTRACT

Method of production of transgenic plants wholly transformed into $T_o$ generation. The method consists of a) genetically transforming a meristem explant; b) selective culturing for the specific development, among all the transformed cells, of those cells giving rise to secondary meristems and/or those cells capable of resulting in neoformed foliar meristems, c) regenerating, from the cellular material obtained during step b), transgenic plants.

14 Claims, 4 Drawing Sheets

OTHER PUBLICATIONS

Figure 1:
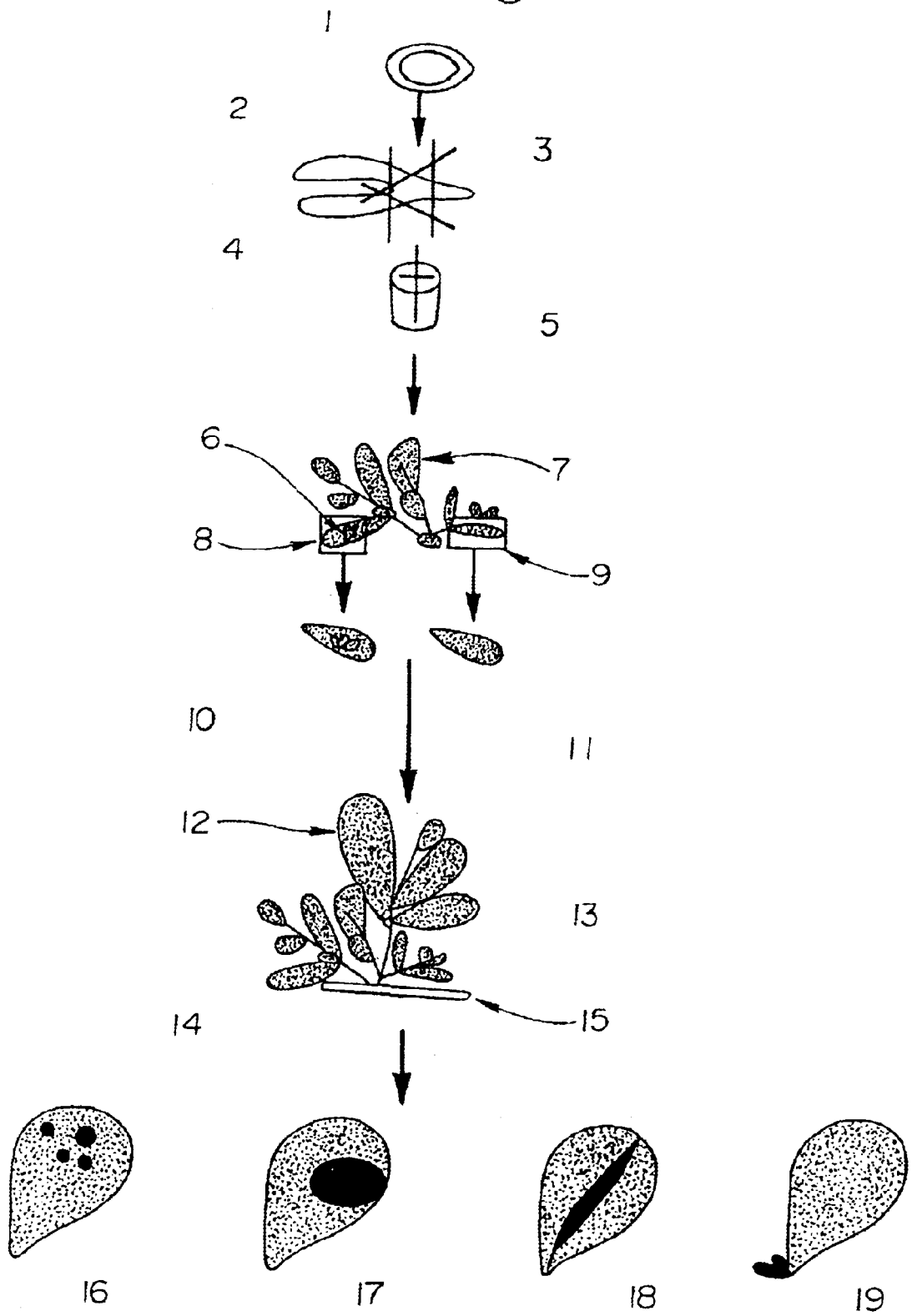

G. Vancanneyt, et al.; "Construction of an intron–containing marker gene: Splicing of the intron in transgenic plants and its use in monitoring early events in Agrobacterium–mediated plant transformation"; *Mol. Gen. Genet.*; 1990; pp. 245–250.

A. Hoekema, et al.; "A binary plant vector strategy based on separation of vir–and T–region of the Agrobacterium tumefaciens Ti–plasmid"; *Nature*; May 12, 1983; vol. 303, pp. 179–180.

Gynheung An; "Development of Plant Promoter Expression Vectors and Their Use for Analysis of Differential Activity of Nopaline Synthase Promoter in Transformed Tobacco Cells"; *Plant Physiol.*; 1986; pp. 86–91.

Richard A. Jefferson; "Assaying Chimeric Genes in Plants: The GUS Gene Fusion System"; *Plant Molecular Biology Reporter*, 1987; vol. 5, No. 4, pp. 387–405.

P.J. Dale, et al.; "Agroinfection of wheat: Inoculation of In Vitro Grown Seedlings and Embryos"; *Plant Sciences*; 1989; pp. 237–245.

Alibert et al., *Sunflower tissue and cell cultures and their use in biotechnology*, Plant Physiol. Biochem., vol. 32(1), pp. 31–44 (1994).

Knittel et al., *Transformation of sunflower (Helianthus annus L.): a reliable protocol*, Plant Cell Reports, vol. 14:81–86 (1994).

Laparra et al., *Expression of foreign genes in sunflower (helianthus annuus L.)—evaluation of three gene transfer methods*, Euphytica, vol 85:63–74 (1995).

\* cited by examiner

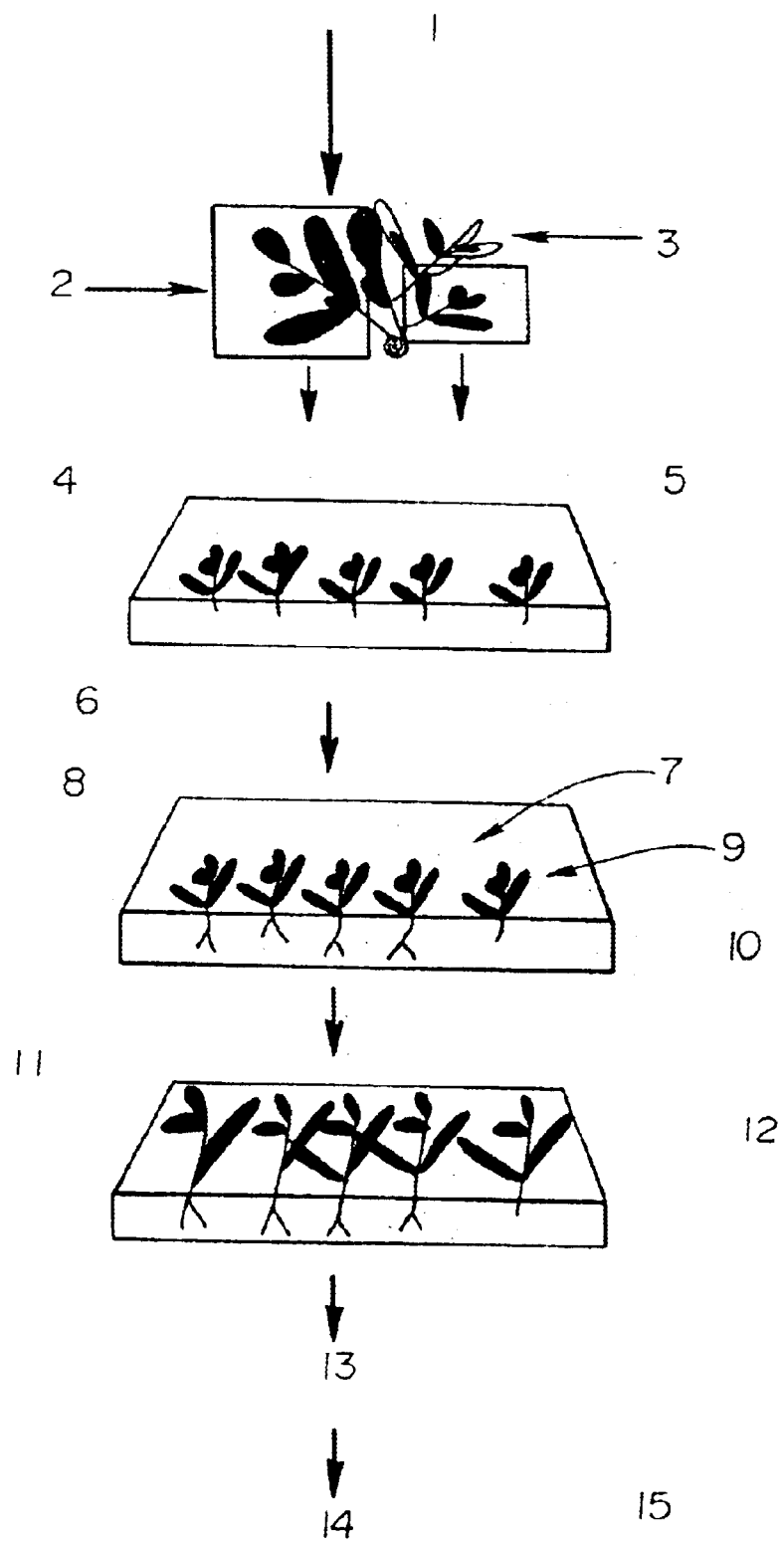

METHOD OF PRODUCTION OF TRANSGENIC PLANTS, WHOLLY PERFORMED IN THE $T_O$ GENERATION, FROM MERISTEMS

This application is a continuation of Ser. No. 08/601,004, filed Jun. 20, 1996, now abandoned, which is a 371 national stage filing of PCT/FR94/01017, filed Aug. 19, 1994, which claims benefit to foreign application 93/103368, filed Aug. 30, 1993 in France.

The present invention relates to a method of production of transgenic plants from meristems, the said plants being wholly transformed in the $T_0$ generation. The invention also relates to the transformed explants obtained during the method.

Genetic engineering techniques are now commonly applied in the breeding of plant species. These techniques allow the introduction of new characters which are difficult or impossible to introduce by conventional techniques. In spite of the development of these techniques, there are however certain species which cannot be easily subjected to transformation or which cannot be regenerated from differentiated explants such as cotyledons or leaves. For these species (for example sunflower, cotton, pea, bean, soybean and the like), it has been demonstrated that these difficulties could, in part, be overcome using, as explant for the transformation, a meristematic explant, for example an apical meristem.

The use of meristems allows the regeneration of fertile plants without a callus formation stage. The technique of regeneration from meristems applies to a large number of different species and, within the same species, to a large number of genotypes. By virtue of this technique, it has been possible for numerous recalcitrant species to be transformed and regenerated (see for example: Bidney et al., Plant Molecular Biol. 18, 301–313, 1992; Bidney et al., Proc. 13e Int. Sunflower Conf. Vol II, Pisa Sept. 1992; Schrammeijer et al., Plant Cell Rep. 9: 55–60, 1990; Christou et al., The Plant Journal, 2(3), 283–290, 1992; Gambley et al., Plant Cell Rep. 12: 343–346, 1993; Russel et al., Plant Cell Rep. 12: 165–169, 1993).

This method has, however, some disadvantages. The transformation frequency is extremely low and the regenerated plants are almost exclusively chimeric, that is to say that some tissues are transformed while others are not. This characteristic results from the fact that the meristem produces the cellular material at the origin of all the tissues of the various plant organs (stem, roots, leaves). Now, regardless of the technique used, the transformation operation only leads to the transformation of a limited number of cells within the explant, these cells being distributed randomly. The meristem is never wholly transformed following such a manipulation. The plants regenerated from a meristem having undergone a transformation stage are therefore chimeric. Wholly transgenic plants are obtained only in the progeny and provided that the germinal line cells have been affected by the transformation. This type of process is described for example in: Bidney et al., Plant Molecular Biol. 18, 301–313, 1992; Schrammeijer et al., Plant Cell Rep. 9: 55–60, 1990.

The disadvantages presented by the production of chimeric plants are recognized in the art, but it has not been possible to offer any solution. A system of labelling which makes it possible to recognize, among the $T_0$ chimeric plants, those which had undergone transformation of the germinal line and which were therefore capable of transmitting the new character to their progeny, has been described (Christou et al., The Plant Journal, 2(3), 283–290, 1992). This method facilitates the production, in the next generation, of wholly transformed plants, but the plants produced in the $T_0$ generation are still chimeric.

Up until now, no method exists which makes it possible to produce in a systematic and predictable manner, transgenic plants, wholly transformed in the $T_0$ generation, from meristematic explants.

The present invention solves this technical problem. The invention is based on the development, by the inventors, of a method which makes it possible to enrich the meristems in transformed cells, in order to arrive at wholly transformed meristems, that is to say meristems all of whose cells are transformed. According to the invention, the regeneration of plants is then carried out exclusively from these wholly transformed explants, which will guarantee the transgenic character of the plants obtained. The inventors have also demonstrated that, under certain conditions, the new formation of newly formed leaf meristems and buds on the leaves of explants derived from meristems can be deduced. The existence of these newly formed leaf buds, containing newly formed leaf meristems, has never been described in the literature. The method of the invention also allows the production of these newly formed leaf meristems in a wholly transformed state. They constitute, in this case, an excellent cellular material for the regeneration of wholly transformed plants in $T_0$.

In general terms, the invention therefore provides a method of production of wholly transformed meristems, and a method which makes it possible to regenerate exclusively from these explants wholly transgenic plants in T0.

More particularly, the invention relates to a method of production of transgenic plants, wholly transformed in the $T_0$ generation, comprising:

a) a stage for the genetic transformation of a meristematic explant, and b) a stage for selective culture which allows the specific development, among all the transformed cells, of those which are at the origin of the secondary meristems and/or of those capable of giving rise to newly formed leaf meristems;

c) the regeneration, from the cellular material obtained during stage ii), of transgenic plants.

Within the context of the present invention, the term "meristematic explant" means an explant consisting essentially or exclusively of meristematic tissue or of tissue capable of becoming, during its development, meristematic. According to the invention, this term covers especially:

an apical meristem (also known in the art as "primary meristem"), particularly an apical stem meristem, that is to say at the origin of the stem;

a newly formed leaf bud;

part of a young leaf capable of giving rise to newly formed leaf buds.

The term "newly formed leaf bud" means a bud carried on the upper epidermis of a leaf. It contains a newly formed leaf meristem. Its development is induced "artificially" by a series of precise culture conditions.

The nature of these various explants will be described later.

The term "secondary meristem" means a meristem derived from a primary meristem. In particular, this term relates, within the context of the invention, to the axillary meristems situated at the axil of the leaves and responsible for the construction of the lateral branches of the plant.

The term "axillary bud" means a bud situated at the axial of a leaf, containing a secondary meristem.

The term "newly formed leaf meristem" means a meristem contained in a new formed leaf bud. The formation of these meristems is caused "artificially" by culture conditions which will be defined later.

At the cellular level, the secondary meristems and the newly formed leaf meristems have a structural organization and an action which are identical to those of the principal meristem, but are smaller in size. Moreover, the newly formed leaf meristems are smaller than the secondary meristems.

The studies leading to the development of the present invention are based on the following morphogenetic principles. The apical meristem contains, at the axil of the leaf Primordia, cells which, in a predetermined manner, will give rise, by cell multiplication, to secondary meristems. These "preprogammed" cells could be transformed during a genetic transformation procedure. The secondary meristems derived from the multiplication of these cells will be composed exclusively of transformed cells. The same is true of the cells which, under favourable culture conditions, will give rise to newly formed leaf meristems. Consequently, the plants regenerated from these transformed secondary meristems and from transformed newly formed leaf meristems will be wholly transgenic.

The inventors have developed a selective culture system which favours the development, among the transformed cells, of those which are at the origin of the secondary meristems and of the newly formed leaf meristems. The other cells will be eliminated.

Preferably, the selective culture comprises the following stages:

i) the culture, on a selective medium, of the meristematic explant having undergone the transformation stage;

ii) the removal of the transformed axially buds and optionally of the transformed newly formed leaf buds, which are obtained during stage i);

iii) the culture, on a selective medium, of the transformed buds obtained according to ii);

iv) repetition, at least one, of stage ii) and iii).

In other words, according to the invention, the explant having undergone the transformation stage is cultured on a selective medium, for a determined time. When shoots and a few leaves appear, the culture is interrupted and the axillary buds and, where appropriate, the newly formed leaf buds, which are at least partially transformed, are removed. The transformed state is recognized by means of the selective marker. The buds are then transplanted and cultured on a selective medium until they produce, in turn, axillary buds and optionally newly formed leaf buds. The culture is interrupted and the transformed buds are again removed and cultured. By repeating this "culture of limited duration/removal of the buds" cycle several times, wholly transformed buds are obtained, in fact, with each cycle, the number of transformed cells in the bud and the proportion of transformed cells relative to the non-transformed cells increases by virtue of cell multiplication. The cycles are therefore repeated until wholly transformed buds are obtained. A wholly transformed bud is recognized by its capacity to produce a shoot which has, throughout, a green colour characteristic of its capacity to withstand inhibition by the selection marker, which corresponds to the transformed state. The regeneration of the transgenic plant is carried out from axillary buds and newly formed leaf buds.

The term "selective agent" means, within the context of the invention, an agent which favours the development of the transformed cells. The selective agent used is normally kanamycin. In this case, the heterologous sequence introduced during the transformation comprises a gene encoding kanamycin resistance, for example NPT II. Kanamycin acts by blocking the chloroplast ribosomes. Consequently, a kanamycin-resistant plant is green because it is capable of making functional chloroplasts, whereas a non-resistant plant shows a yellow or white colour characteristic of the absence of functional chloroplasts. This phenomenon allows the visual selection of the transformants. The green newly formed leaf buds and the green axillary bus are selected; the principal bud, the principal plantlet and all the parts of the plant which are white or yellow are removed.

The removal of the principal bud favours the development of the axillary buds, particularly when a species exhibiting apical dominance, such as improved sunflower, is involved.

The number of selective culture cycles is preferably at least 2, including the first culture of the meristematic explant which has undergone the transformation stage. The number of cycles should be sufficient in order to allow the production of wholly transformed buds. Typically, 3 cycles should be applied, but it may be necessary, with some species or with some transformation techniques, to perform more, for example 4, 5, or 6 cycles.

In general, each stage of culture on selective medium lasts for about 15 days, but can vary between 1 and 3 weeks, depending on the species. The duration of each culture stage should be sufficient to allow the appearance of shoots having at least one leaf. If the selection cycle is repeated 3 times, the total duration of the selective culture stage will be about 6 weeks, the selective agent being present during the whole of this period. Where appropriate, a reporter gene, for example GUS, may also be incorporated during the transformation in order to allow analysis of the transformation state.

The efficiency of the method of the present invention is unexpected since the duration of the entire selective culture stages according to the invention is substantially longer than that usually applied (for example 6 weeks instead of 2 weeks). Now, it has been indicated by several authors that kanamycin has damaging effects on the regeneration of the plant (Schrammeijer et al., Plant Cell Rep. 9: 55–60, 1990). The transformation and regeneration methods developed up until now therefore tended to minimize the duration of the selection stage (Bidney et al., Proc. 13e Int. Sunflower Conf. Vol II, Pisa Sept. 1992). In fact, the present inventors have demonstrated that a prolonged period of selective culture on kanamycin exerts no inhibitory effect on the regeneration of the plant, contrary to what is indicated in the literature.

As regards the meristematic explant transformation stage, any appropriate technique can be used. This stage comprises bringing the meristematic explant into contact with Agrobacterium containing a heterologous sequence intended to be introduced into the plant cells, under conditions allowing the transfer of DNA.

There may be mentioned as example of a transformation technique the bombardment of the meristematic explant with microparticles, the bringing of the explant into contact with Agrobacterium being carried out either simultaneously, or after the bombardment. This technique makes it possible to carry out a large number of microwounds on the explant, which is necessary for the transfer of DNA by Agrobacterium. In the case of a bombardment and a simultaneous transformation, the microparticles are coated with Agrobacterium (EP-A-0,486,234). Preferably, the bringing into contact with Agrobacterium is carried out following the bombardment by applying, for example, the technique used in EP-A-0,486,233. The microparticles normally consist of gold or tungsten.

Another transformation technique consists in bringing the meristematic explant into contact with a suspension of Agrobacterium. In this case, it is preferably to make wounds on the explant, for example, by cutting it with a scalpel, in order to facilitate the transformation.

The transformation stage also comprises a period of coculturing the explant with Agrobacterium. This has a of a duration of 2 to 4 days, 3 days being preferred. The coculture medium may be any medium normally used for this purpose. A particularly advantageous medium is the M2 medium supplemented with BAP, as described in the examples below.

The Agrobacterium is normally *Agrobacterium tumefaciens*. Various strains may be used, for example the strain GV2260 or LBA 4404. As vector, there may be mentioned the binary plasmid pGA 492-GI, or alternatively the p35GUS intron. The "strain/vectors" pair may influence the efficiency of the transformation. It is preferable to use the strain LBA 4404 with the vector pGA 492-GI.

The nucleic acid sequence intended to be introduced into the plant cells contains any sequence capable of conferring on the plant traits of agronomic interest. Thee may be mentioned, as example, a sequence which confers resistance to insects, to herbicides or to fungal diseases (for example *Sclerotinia sclerotorium* or *Botrytis cinerea*, one or more genes for storage proteins of seeds, or which improve the quality of the storage proteins, sequences which modify the maturation of fruit, sequences which confer resistance to viruses, one or more ribozymes, one or more antisense sequences, one or more genes involved in the metabolism of fatty acids or of amino acids or one or more genes involved in male sterility.

In addition, the heterologous sequence also comprises a sequence encoding an agent which allows the selection of the transformants, for example an agent which confers resistance to an antibiotic such as kanaymcin, G418 or neomycin. The vector comprises the regulatory sequences necessary for the stable expression of the heterologous sequence. As promoter, there may be mentioned the 35S promoter, the double 35S with the translation enhancer $\Omega$ or the ubiquitin promoter derived from sunflower. The NOS terminator is particularly preferred.

The transformation and selective culture stages described above form part of a set of operations which make it possible, starting with the explant, to regenerate transgenic plants. The method of the invention, in its entirety, can be summarized as follows:

2. Carrying out of the explant transformation stage as described above;

3. Carrying out of the series of selection stages as outlined above;

4. Regeneration of transgenic plants from the structures obtained at the end of the selection cycles.

According to the method of the invention, the preparation of the meristematic explant consists in a stage for preculturing an apical meristem, or an apical semimeristem, for 5 to 30 days, preferably between 5 and 8 days.

The preculture medium is a plant cell culture medium supplemented with cytokinin and more particularly with 6-benzylaminopurine (designated hereinafter as BAP). Preferably, the medium is MS (Murashige-Skoog) medium supplemented with 0.05 to 2.0 mg/l BAP, for example 0.1 mg/l of BAP, without any other hormone.

The inventors have demonstrated that the preculture stage and its duration exert a substantial influence on the development of the explant. When its duration is greater than 9 to 10 days, newly formed leaf buds appear on the leaves. The shoots regenerated on the apical meristem have, in this case, leaves which carry newly formed leaf buds on the upper epidermis.

According to this variant of the invention, it is possible, before the transformation stage, to excise the newly formed leaf buds or even simply to remove pieces of leaf, and to use them in the transformation stage. According to this embodiment of the invention, the meristematic explant subjected to the transformation may therefore consist either of part of a leaf obtained after at least 9 days of preculture capable of giving newly formed leaf buds, or of excised newly formed leaf buds.

In the case where the preculture lasts between 5 and 12 days, the apical meristem normally serves directly as meristematic explant in the transformation stage. In this case, the newly formed leaf buds are induced during the preculture stage itself, but appear only during the subsequent development, for example during the coculture or during the culture on a selective medium.

According to the invention, the same culture medium can be used for the preculture, coculture and selection stages. This medium is preferably the MS medium supplemented with BAP at a concentration of 0.05 to 2.0 mg/l, preferably 0.1 mg/l. Normally, the BAP is the only plant hormone present in the medium. In particular, it is preferable that this medium does not contain either gibberellic acid or indoleacetic acid, particularly when the preculture medium is involved. The medium may also be supplemented, during the preculture and coculture stages, with a phenolic compound, for example, acetosyringone which is capable of activating the Agrobacterium vir genes. A concentration of about 200 $\mu$M is appropriate. For the selective culture stage, the medium contains at least one selective agent, advantageously kanamycin, at a concentration of between 50 and 200 mg/l, preferably 50 mg/l, and optionally, bacteriostatic agents.

The apical meristems are obtained by germination of decorticated and sterilized ripe seeds. The method of germination typically consists in culturing the seeds on a preferably solidified germination medium, for example the MS medium whose macro- and microelements are optionally reduced by half. The duration of the germination is between 2 and 4 days, preferably 4 days, at 25° C., preferably with a photoperiod of about 16 hours.

After the preculture, transformation and selection stages, a regeneration stage is carried out starting with the wholly transformed shoots and buds. The culture media and the conditions are those usually applied in the art for the species in question. For sunflower, the regeneration conditions are indicated in the examples below.

In addition to the method of production of transgenic plants described above, the invention also relates to the newly formed leaf buds and the wholly transformed secondary meristems obtained during the method. It also relates to the transgenic plants wholly transformed in the $T_0$ generation which are obtained from the meristematic explants.

The method of the invention exhibits numerous advantages. It is especially more efficient than the prior art techniques since the regeneration is carried out only if the explant is wholly transformed. The existing techniques involved, on the other hand, the regeneration of all the meristems which have undergone the transformation operation, followed by the selection, among the chimeric plants obtained, of those whose germinal line had been transformed. The method of the invention therefore allows a substantial economy in time and means.

Furthermore, the yield, of transgenic plants, obtained according to this method is considerably higher than that obtained according to previous techniques. For example, for sunflower, 92% of the regenerated plants give at least one transgenic plant in the progeny (Table 8 below). This figure should be compared with 0.2% to 2% which is reported by Bidney et al., Plant Molecular Biol. 18, 301–313, 1992.

The method of the invention applies to numerous plants species and more particularly to dicotyledons, especially to those which are difficult to transform and to regenerate. There may be mentioned, as example, cotton, soy bean, oleaginous plant species, for example sunflower, species belonging to the family of leguminous plants, for example pea, bean or alternatively species belonging to the Cucurbitaceae family, for example courgette. Within these species, numerous different genotypes can be used. Sunflower is particularly preferred.

Various aspects of the invention are illustrated in the figures:

FIG. 1 shows the procedure for the transformation of leaves derived from semimeristems for analyzing the expression of Glucuronidase in the axially shoots regenerated from newly formed leaf buds.

Legend:
1—seed
2—germination medium M0, 2 days
3—dissection of the apices: removal of the cotyledons, the radicle and the first leaf
4—sectioning of the apex into two halves
5—preculture of the semimeristems on M2 medium containing acetosyringone at 200 µM for 30 days
6—newly formed leaf bud
7—axillary shoots induced from semimeristems
8—removal of the leaves carrying newly formed leaf buds initiated on the upper face
9—removal of the leaves without newly formed leaf bud
10—bombardment and 3 days of coculturing with *Agrobacterium tumefaciens* of the leaves on M2 medium containing acetosyringone at 200 µM
11—culture on the M2 medium containing augmentin at 400 mg/l for 15 days
12—axillary shoots
13—development of newly formed leaf buds into axillary shoots
14—analyses of the expression of glucuronidase in the axillary shoots induced from newly formed leaf buds which appeared on the leaves
15—leaf explant
16—spots of transformed cells GUS+
17—transformed cell regions GUS+
18—transformed cell lines GUS+
19—transformed axillary buds GUS+

Figure 2:
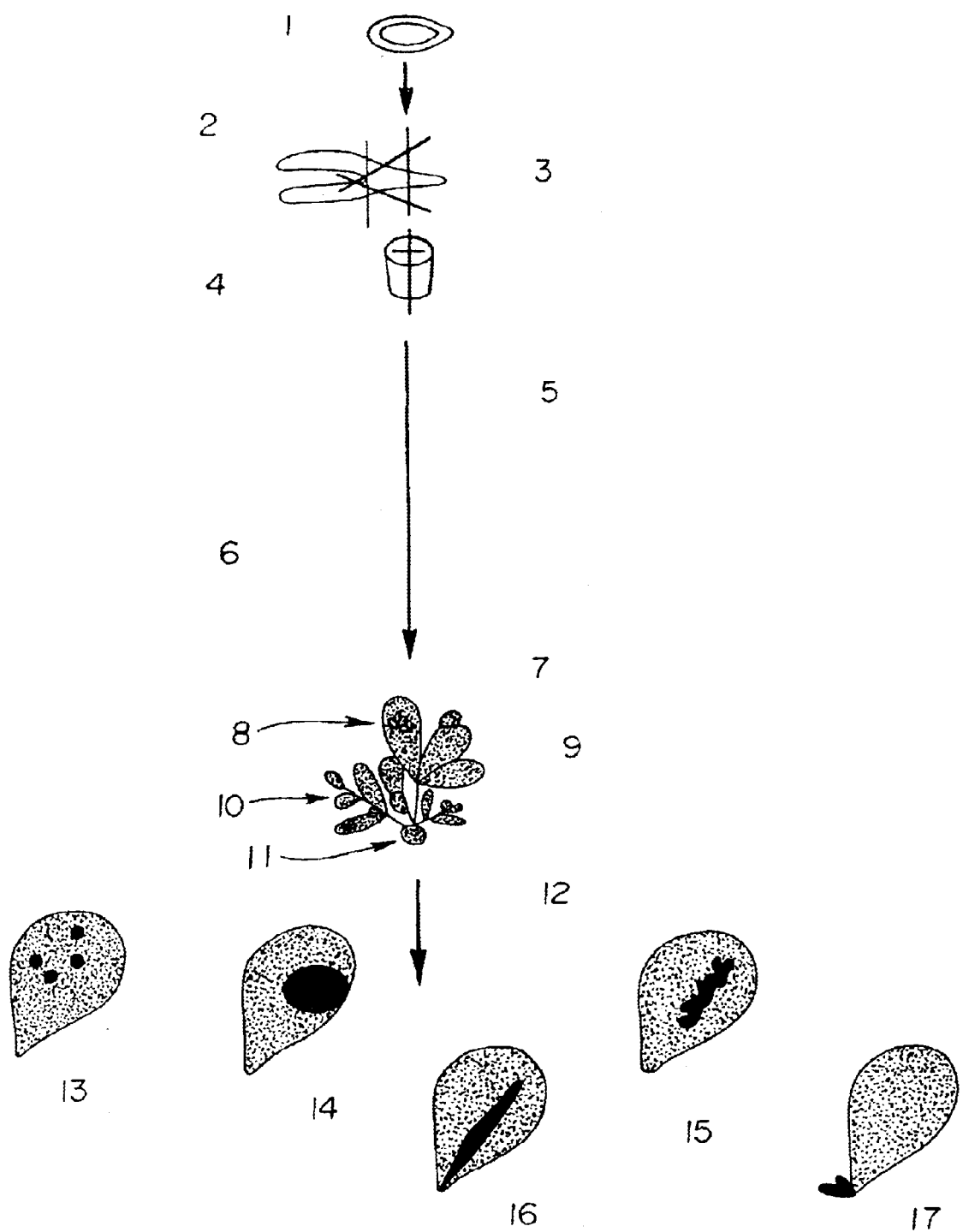

FIG. 2 shows the procedure for the transformation of semimeristems for analyzing the expression of Glucuronidase.

Legend:
1—seed
2—germination medium M0, 2 days
3—dissection of the apices: removal of the cotyledons, the radicle and the first leaf
4—sectioning of the apex into two halves
5—preculture of the semimeristems on M2 medium containing acetosyringone at 200 µM for 5 days
6—bombardment and 3 days of coculturing with *Agrobacterium tumefaciens* of the semimeristems on M2 medium containing acetosyringone at 200 µM
7—culture of the bombarded and cocultured semimeristems on M2 medium containing augmentin at 400 mg/l for 15days
8—newly formed leaf bud
9—axillary shoots induced from the semimeristems
10—axillary shoot
11—callus at the base
12—analyses of the expression of glucuronidase in the axillary shoots induced from semimeristems
13—spots of transformed cells GUS+
14—transformed cell regions GUS+
15—transformed newly formed leaf buds GUS+
16—transformed cell lines GUS+
17—transformed axillary buds GUS+

Figure 3:
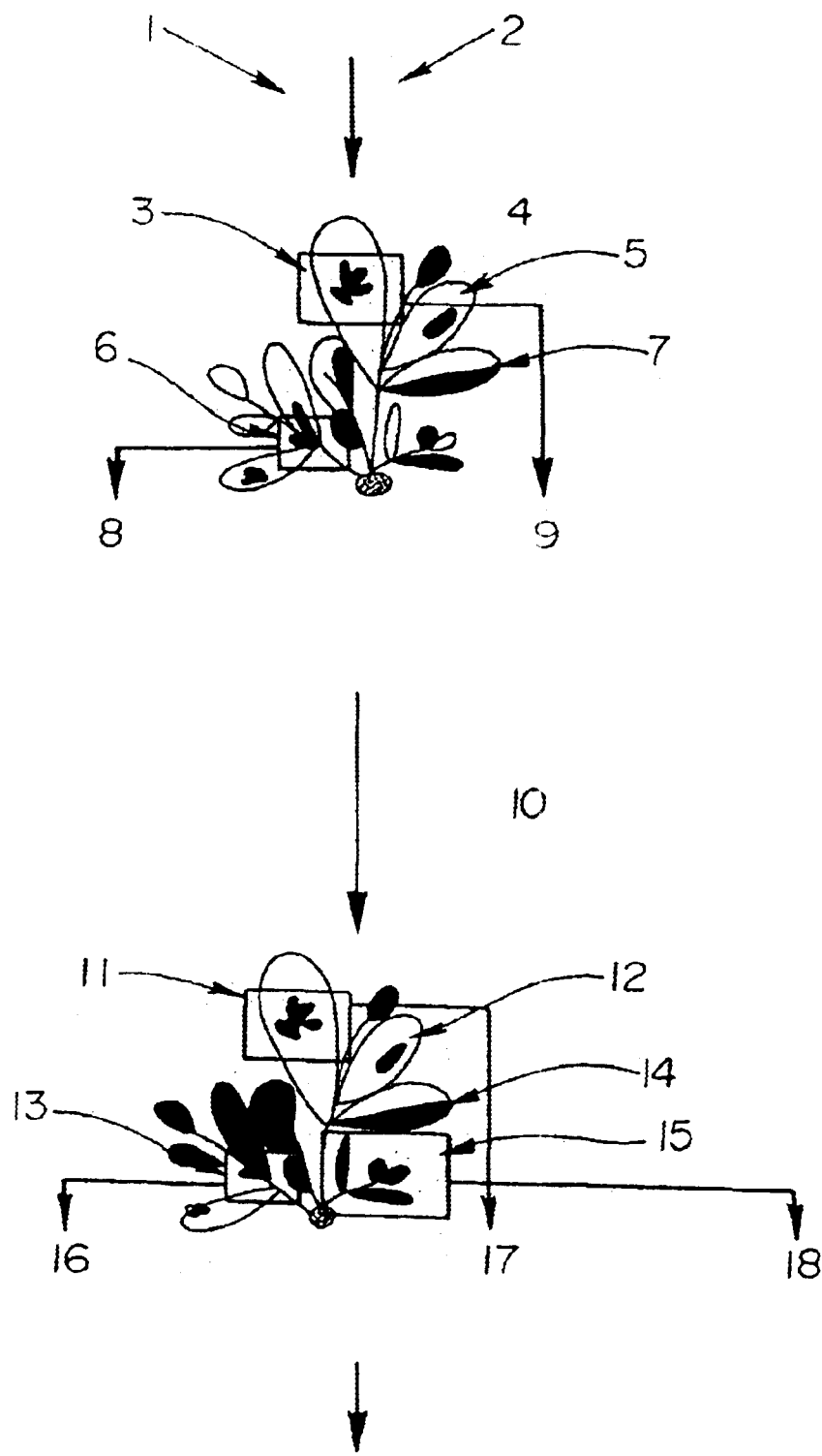

FIG. 3 shows the selection of axillary shoots transformed and regenerated from newly formed leaf buds on the leaves or from semimeristems.

Legend:
1—semimeristems bombarded and cocultured according to the procedure defined in Example 2
2—semimeristem-derived leaves bombarded and cocultured according to the procedure defined in Example 1
First selection culture on kanamycin:
3—green newly formed leaf bud resistant to kanamycin
4—culture of the explants on M2 medium containing augmentin at 400 mg/l and kanamycin at 50 mg/l for 15 days
5—non-transformed white part sensitive to kanamycin
6—green auxiliary bud resistant to kanamycin
7—transformed green part resistant to kanamycin
8—removal of the green axillary buds
9—removal of the green newly formed leaf buds
Second selection culture on kanamycin:
10—culture of the green axillary buds, of the green newly formed leaf buds and of the green axillary shoots on M2 medium containing augmentin at 400 mg/l and kanamycin at 50 mg/l for 15 days.
11—green newly formed leaf bud resistant to kanamycin
12—non-transformed white part sensitive to kanamycin
13—green axillary bud resistant to kanamycin
14—green part resistant to kanamycin
15—green axillary shoot resistant to kanamycin
16—removal of the green axillary buds
17—removal of the green newly formed leaf buds
18—removal of the green axillary shoots FIG. 4 shows the regeneration of transformed plants.
Legend:
Third selection culture on kanamycin:
1—culture of the green axillary buds, the green newly formed leaf buds and the green axillary shoots on M2 medium containing augmentin at 400 mg/l and kanamycin at 50 mg/l for 15 days
2—Removal of the green axillary shoots
3—chimeric axillary shoot with non-transformed white parts and transformed green parts
4—culture in the SORBAROD system supplemented with M3 medium for 30 days in a culture chamber
5—taking root
6—washing of the M3 medium, addition of M4 medium
7—plant which has taken root 8—culture in the SORBAROD system for 10 days in the culture chamber
9—plant which has not taken root
10—development
11—culture in the SORBAROD system in a greenhouse for 10 days
12—development and acclimitization
13—transplanting the plants which have taken root in peat in pots, grafting the plants which have not taken root onto rootstocks, culture in a greenhouse
14—flowering and self-pollination
15—growth

EXAMPLE 1

Transformation of leaves derived from semimeristems for analyzing the expression of glucuronidase in the shoots regenerated from newly formed leaf buds (FIG. 1)

1.1—Preparation of the semimeristems

The seeds of sunflower (*Helianthus annuus*) of the lines (Ha300, RHa 274, RHa 297, RHa 356, RHa 359, RHa 362), two populations LG60 and LG61 derived from interspecific crossings with *Helianthus petiolaris*, and several lines provided by LIMAGRAIN GENETICS (Les Alleuds) are used for these experiments. The seeds are decorticated in order to remove the teguments, and then sterilized for 20 minutes in Javelle water at 12° chlorine strength supplemented with 1 ml/l of Tween 80. The decorticated seeds are then rinsed 5 times with sterile distilled water. The seeds are then steeped in sterile distilled water for 1 hour and then the film covering the seed is removed. The bare seeds are again sterilized for 2 minutes in Javelle water at 6° chlorine strength, rinsed 3 times with sterile distilled water and dried on filter paper in a laminar flow cabinet. The dry seeds are then allowed to germinate on MO medium: macroelements, microelements, Fe-EDTA and vitamins of the MS medium (Murashige and Skoog, 1962—Physiologia Plantarum, 15: 473–497) supplemented with 10 g/l of sucrose, 7 g/l of agar, pH 5.8, and they are allowed to germinate in a culture chamber at 26° with 16 h of light (50$\mu$ Einstein/m2 of light intensity), for two days. The germinated seeds are removed, the cotyledons and the radicles are removed as well as the apical part of the apex. The cylinder, a few millimeters in diameter, thus obtained is then cut into two halves in the axis of the cotyledonary insertions. This explant containing an apical semimeristem is called a semimeristem.

1.2—Culture of the semimeristems

The semimeristems are then cultured in M2 medium (macroelements, microelements, Fe-EDTA and vitamins of the MS medium) supplemented with 10 g/l of sucrose, 0.1 mg/l of BAP, 8 g/l of agar, pH: 5.8 to 6) containing 200 $\mu$M of acetosyringone for 30 days in a culture room at 26° C. with 16 h of light (50$\mu$ Einstein/m2 of light intensity). During this culture period, the semimeristems develop shoots derived from the secondary meristems at the axil of the leaf primordia. After 10 days of culture, protuberances appear at the upper face of the leaves. These protuberances, which are newly formed leaf meristems, are transformed into newly formed leaf buds (FIG. 1). These buds are derived from new formations of vegetative meristems from the epidermal and subepidermal cells of the upper face of the leaves.

After 30 days of culture, the leaves having secondary meristems or newly formed leaf buds and the leaves without newly formed leaf buds are removed (FIG. 1).

1.3—Bombardment and coculture of the leaves derived from semimeristems.

These leaves are bombarded with a helium particle gum (Particle Inflow Gun, PIG) (FINER et al., 1992—Plant Cell Reports, 11: 323–328) with tungsten particles (0.2 $\mu$m to 2 $\mu$m in diameter) in order to make microwounds on the explants.

The tungsten particles (50 mg) are sterilized in 500 $\mu$l of 95% ethanol for 20 min and then rinsed 4 times by centrifugation in sterile water (10,000 rpm for 1 min). The sterile particles are taken up in 300 $\mu$l of TE buffer (10 mM Tris HCl, 1 mM EDTA). A volume of 2 $\mu$l of bare particles is used for each bombardment. The leaves are placed with the upper face facing upwards on a Petri dish 5 cm in diameter containing water with agar at 15 g/l. The Petri dishes containing the explants are placed in the gun chamber and a vacuum of 29 inches of Hg is made. The bombardment of the particles is made with a pressure of 8 bar at a distance of 16 cm between the gun and the explants to be bombarded.

The bombarded explants are then placed in a Petri dish 9 cm in diameter containing M2 medium supplemented with 200 $\mu$M acetosyringone. One drop (1 to 10 $\mu$l) of the suspension of disarmed *Agrobacterium tumefaciens* LBA 4404 (HOEKEMA et al., 1983—Nature, 303: 179–180) obtained from an overnight culture at an optical density Od=2 to 600 nm is deposited on the explant. The LBA 4404 strain contains the binary vector pGA492-GI (AN, 1986—Plant Physiol., 81: 86–91) which carries the NPT II gene conferring the resistance to kanamycin under the control of the pNOS promoter (HERRERA-ESTRELLA et al, 1983—EMBO J., 2: 987–995) and the t-NOS terminator (DEPICKER et al., 1982—Mol. Appl. Genet., 1: 561–573) into which the GUS intron gene has been inserted at the ScaI site under the control of the CaMV p35S promoter and the t-NOS terminator (VANCANNEYT et al., 1990—Mol. Gen. Genet., 220: 245–250). The explants bombarded and inoculated with *Agrobacterium tumefaciens* are cocultured for 3 days at 26° C. with 16 h of light (50$\mu$ of Einstein/m$^2$). The combination of the bombardment with bare particles and the coculture with *Agrobacterium tumefaciens* makes it possible to cause by the bombardment microwounds in the cells of the leaves and in the secondary meristems. These microwounds allow the penetration of the bacterium and a greater transformation efficiency according to the method Bidney et al., 1992 (Plant Mol Biol., 18: 301–313).

1.4—Culture of the leaves and regeneration of shoots from newly formed leaf buds After the coculture, the explants are transplanted in a Petri dish containing M2 medium supplemented with augmentin at 400 mg/l and placed for 15 days in a culture chamber (16 h of light, 15$\mu$ Einstein/m2, 23° C. and 8 h of darkness, 21° C.).

After 15 days of culture, the newly formed leaf buds which have appeared or which are already present on the bombarded and cocultured leaves developed into shoots having 1 to 5 leaves and a short stem. These shoots are separated and placed in a buffer for analyzing the glucuronidase activity (FIG. 1).

1.5—Analysis of the glucuronidase activity in the shoots derived from newly formed leaf buds.

The shoots derived from newly formed leaf buds are immersed in a GUS buffer containing 1 mg/ml of X-gluc. (5-bromo-4-chloro-3-indolyl-$\beta$-D-glucuronic acid cyclohexylammonium) (JEFFERSON, 1987—Plant Mol. Biol. Rep., 5: 387–405) infiltrated under vacuum and incubated for 24 h at 37° C. in darkness.

After incubating for 24 h, the transformed cells which have expressed the GUS gene, possess a glucuronidase activity (noted GUS+activity), are capable of hydrolyzing X-Glu and liberate a blue-coloured compound.

Various types of plaques of transformed cells having a GUS+activity are visible after an incubation of 24 h (FIG. 1).

Spots few millimeters in diameter, located at the surface of the leaves of the shoots regenerated from newly formed leaf meristems. These spots are derived from newly formed leaf meristem cells transformed at the time of the bombardment and of the coculture.

Large areas of transformed cells which could be either blue discs with a diameter greater than 5 mm or blue half-leaves, or blue cell lines. These large areas are derived from transformed cells situated inside the meristems of the newly formed leaf buds which give wholly transformed cellular progenies (half-leaves—discs and cell lines).

In some cases, blue secondary meristems or buds expressing glucuronidase are observed at the axil of the leaves of the shoots. These secondary meristems are wholly transformed. They are derived either from inner cells of the bombarded and cocultured newly formed leaf meristems which have given, during growth and differentiation, an axillary bud at the axil of a leaf, or from transformed cells at the surface of the leaf which has newly formed newly-formed leaf meristems and then a secondary bud.

The results of Table 1 illustrate the percentage of bombarded and cocultured leaves which gave shoots having either spots of GUS+cells, or large areas of GUS+cells, or GUS secondary meristems. Most of the bombarded leaf explants regenerate shoots from newly formed leaf buds which contain GUS+spots (80%), and large GUS+areas (55%). These shoots are chimeric plantlets composed of a mixture of transformed and non-transformed cells.

| Percentage of bombarded and cocultured explants having: | | |
|---|---|---|
| GUS+ spots | large GUS+ areas | axillary buds |
| 80 | 55 | 2 |

These shoots will give a genetically transformed progeny only if transformed cells exist in the region of the meristem containing the germinal cells at the origin of the ovules or of the pollen grains. On the other hand, 2% of the bombarded and cocultured leaf explants contain transformed axillary buds situated at the axil of the leaves carried by the shoots derived from newly formed leaf buds. The unicellular origin of these axillary buds implies that they are wholly transformed and will give a progeny of transformed plants according to the Mendelian segregation (at least ¾ of transformed plants and ¼ of non-transformed plants).

EXAMPLE 2

Transformation of semimeristems for analyzing the expression of glucuronidase in the shoots regenerated from semimeristems (FIG. 2)

2.1. Preparation of the semimeristems

The preparation of the semimeristems is identical to that presented in Example 1 (part 1.1)

2.2 Preculture of the semimeristems

The semimeristems are precultured for 1, 5, 8 and 12 days in M2 medium containing acetosyringone at 200 μM at 26° C. with 16 h of light (15μ Einstein/m²).

After the preculture, the semimeristems form small shoots which developed from the secondary meristems and from the apical meristem. The development of these shoots depends on the duration of the preculture. The longer the period of preculture, the more developed the shoots. At 12 days of preculture, the shoots carry leaves and newly formed leaf buds at the upper surface of the leaves (FIG. 2).

2.3—Bombardment and coculture of the precultured semimeristems

After the preculture, the semimeristems are bombarded and cocultured according to the procedure described in Example 1 part 1.3.

2.4—Culture of the bombarded and cocultured semimeristems

Once the semimeristems have been precultured, bombarded and cocultured, they are cultured in Petri dishes 9 cm in diameter containing M2 medium supplemented with 400 mg/l of augmentin and placed in a culture chamber (16 h of light, 15μ Einstein/m², 23° C. and 8 h of darkness, 21° C.).

After 15 days of culture, several shoots having 1 to 5 leaves and a stem develop from the axillary buds, from the apical meristem and also from the newly formed leaf buds which appeared at the upper surface of the leaves.

2.5—Analyses of the glucuronidase activity in the shoots derived from the semimeristems (FIG. 2)

The shoots formed from the semimeristems are separated and analysed for the expression of glucuronidase activity. The conditions of the test for the glucuronidase activity are described in Example 1 part 1.5. Plaques of cells having glucuronidase activity are observed (FIG. 2):

blue spots of transformed cells expressing glucuronidase (GUS+)

large areas or cell lines expressing glucuronidase (GUS+)

secondary meristems at the axil of the leaves which are completely blue, expressing glucuronidase (GUS+)

furthermore, in the case of the transformations of precultured semimeristems (1 to 12 days) GUS+transformed newly formed leaf buds appear at the upper face of the leaves (FIG. 2). These newly formed leaf buds are derived from transformed cells located on the young leaves at the time of the bombardment and of the coculture of the semimeristem. These cells then developed into newly formed leaf buds. The unicellular origin of these newly formed leaf buds makes it possible to obtain wholly transformed buds which will give wholly transformed plants.

| Duration of preculture | Percentage of bombarded and cocultured semimeristems having: | | |
|---|---|---|---|
| | GUS+ cell spots | large GUS+ areas | GUS+ axillary buds |
| 1 day | 38 | 26 | 0 |
| 5 days | 50 | 40 | 4 |
| 8 days | 67 | 47 | 0 |
| 12 days | 38 | 38 | 0 |

The transformation frequencies obtained by bombardment of semimeristems are high, 38 to 70% of bombarded and cocultured semimeristems have GUS+spots and 26 to 47% have large GUS+areas (Table 2).

The percentages of bombarded and cocultured semimeristems having large GUS+areas are higher when the semimeristems are precultured for 5 days (40%) and for 8 days (47%) (Table 2).

Only the semimeristems precultured for 5 days gave shoots with completely blue newly formed leaf or axillary buds.

These wholly transformed newly formed leaf or axillary buds will give wholly transformed plants whose progeny will be at least ¾ transformed plants and ¼ non-transformed plants. A preculture duration of 5 days is therefore the optimum duration for the standard procedure described in this invention.

EXAMPLE 3

Transformation of semimeristems or of leaves derived from semimeristems (FIGS. 3 and 4)

3.1—Transformation of leaves derived from semimeristems.

The preparation and the preculture of the semimeristems, the bombardment and the coculture of the leaves derived from the semimeristems are performed according to the procedure described in Example 1 (parts 1.1, 1.2 and 1.3)

3.2—Transformation of semimeristems

The preparation, the preculture, the bombardment and the coculture of the semimeristems is performed according to the procedure described in Example 2 (parts 2.1, 2.2, 2.3).

3.3—Selection of the shoots resistant to kanamycin 3.3.1—First selection culture in the presence of kanamycin (FIG. 3)

After the coculture, the explants (semimeristems or leaves) are placed in a Petri dish 9 cm in diameter containing the M2 medium supplemented with 400 mg/l of augmentin and 50, 100, 200 and 400 mg/l of kanamycin.

The dishes containing the explants are placed in a culture chamber (16 h of light, 15$\mu$ Einstein/m2, 23° C. and 8 h of darkness, 21° C.) for 15 days of culture. During this culture, the explants develop, giving shoots having 1 to 5 leaves and a short stem (FIG. 3).

After 15 days of culture on the selective medium containing kanamycin, the appearance of the regenerated shoots are different depending on the quantity of kanamycin-resistant transformed cells constituting them:

shoots carrying leaves with white or yellow areas composed of non-transformed cells sensitive to kanamycin and green areas composed of transformed cells resistant to kanamycin.

shoots carrying green axillary buds at the axil of the leaves undergoing development. These green axillary buds are transformed and develop into axillary shoots in the presence of kanamycin.

shoots carrying on their leaves non-transformed yellow or white newly formed leaf buds sensitive to kanamycin.

non-transformed completely white or yellow shoots sensitive to kanamycin.

shoots carrying on the leaves of the green newly formed leaf meristems or buds undergoing development, resistant to kanamycin.

3.3.2—Second selection culture in the presence of kanamycin (FIG. 3)

The green axillary shoots, the green axillary buds and the green newly formed leaf buds or meristems are replanted on the M2 medium containing augmentin at 400 mg/l and kanamycin (50-100-200 and 400 mg/l) and incubated under the same culture conditions as above (part 3.3.1) for 15 days.

After this period of culture, the newly formed leaf buds and axillary buds again developed shoots (FIG. 3)

some non-transformed shoots are completely white, indicating sensitivity to kanamycin.

some shoots have leaves carrying green parts composed of transformed cells resistant to kanamycin and white parts composed of non-transformed cells sensitive to kanamycin.

The presence of shoots which are not wholly transformed indicates that at the end of the first culture, all the green newly formed leaf buds and axillary buds were not wholly transformed and gave rise to chimeric shoots composed of a mixture of transformed and non-transformed cells.

some chimeric shoots have green axillary buds or secondary meristems resistant to kanamycin.

some chimeric shoots have leaves with green plaques and white plaques which carry green newly formed leaf meristems or buds resistant to kanamycin.

some shoots have green leaves carrying green secondary meristems or axillary buds. These shoots which are composed of transformed cells are resistant to kanamycin.

These completely green shoots which are derived from newly formed leaf meristems or buds develop. These shoots are composed of a large number of transformed cells resistant to kanamycin.

In the shoots obtained at the end of the second culture, a number of completely green shoots are observed whereas at the end of the first culture, no completely green shoot was observed, indicating that some newly formed leaf or axillary buds cultured in the second culture in the presence of kanamcyin were wholly transformed.

3.3.3—Third selection culture in the presence of kanamycin (FIG. 4)

The completely green shoots, the green axillary buds, and the green newly formed leaf meristems or buds are separated and replanted in the M2 medium and cultured as above (part 3.3.1) (FIGS. 3 and 4).

After 15 days of culture, shoots developed from these explants. Most of the shoots are completely green and develop rapidly on the M2 medium containing kanamycin. These shoots are wholly transformed. A small number of shoots still have green plaques and plaques of white cells. These chimeric shoots are eliminated (FIG. 4).

Only the green shoots are replanted in a SORBAROD culture system. The SORBAROD culture system consists of a closed and sterile mini-greenhouse containing cellulose cylinders moistened with M3 medium (macroelements, microelements, Fe-EDTA and vitamins of the MS medium) supplemented with 10 g/l of sucrose. The mini-greenhouse is perforated with 3 orifices covered with a membrane providing the gas exchanges and equilibrating the internal relative humidity with the external relative humidity.

The green shoots derived from the third culture are planted in cellulose cylinders and installed in the SORBAROD mini-greenhouses (FIG. 4). The mini-greenhouses are placed in a culture chamber (16 h of light, 23° C., 15$\mu$ Einstein/m², and 8 h of darkness, 21° C.). After incubating for 30 days, the transformed plants take root and develop. The M3 medium is then removed by pipetting and the cylinders are rinsed 3 times with sterile distilled water and then the cylinders are moistened with M4 medium (macroelements, microelements, Fe-EDTA and vitamins of the MS medium) fee of sucrose. After 10 days of culture in a culture chamber, the plants develop large leaves and reach a size of 2 to 3 cm. The SORBAROD mini-greenhouses are transferred into a greenhouse (temperature 26° C.—photoperiod (16 h/8 h) for 10 days. During this period, the plants which have taken root develop and become acclimatized to the greenhouse conditions. Next, the cylinders carrying the sunflower plants which have developed roots and leaves are placed in pots containing peat sprayed with a COIC and LESAINT type solution (1971—Hortic. Fr., 8: 11).

The plants which have not taken root are grafted onto stems of rootstocks (non-transformed sunflower, 4 to 6 leaf stage after emergence). The base of the stem of the transformed plant is bevelled and placed in a recess made in the stem of the rootstock. The graft is attached to the rootstock by a raffia link and surrounded by a plastic bag. After the graft has taken, the leaves and the stem develop and the plastic bag is removed. The rootstocks and the grafts are then transferred to a greenhouse with spraying with the COIC and LESAINT type nutrient solution (1971—Hortic. Fr., 8: 11).

The sunflower plants grow, flower and are self-pollinated. The seeds from each transformed plant are harvested for analysis of segregation of the kanamycin resistance gene and the GUS gene (see, Example 8).

EXAMPLE 4

Influence of the bacterial strain and the binary plasmid on the efficiency of genetic transformation of the leaves derived from semimeristems The leaves derived from semimeristems are bombarded and cocultured with various strains:

LBA 4404 containing the binary plasmid PGA 492-GI (described in Example 1, part 1.3)

GV 2260 containing the binary plasmid p35S GUS intron (VANCANNEYT et al., 1990—Mol. Gen. Genet, 220: 245–250)

C58'3 (MULLINEAU et al, 1989—Plant Sci, 63: 237–245) containing the plasmid pGA 492-GI (Cf Example 1, part 1.3).

After culturing the leaves for 6 weeks (according to the procedure described in Example 3) on selective medium containing 100 mg/l or 200 mg/l of kanamycin, the kanamycin-resistant green shoots are subjected to a test for the expression of glucuronidase activity. When the cells express glucuronidase activity, this activity is noted GUS+ activity. The procedure for testing glucuronidase activity is described in Example 1, part 1.5.

The results are presented in Table 3.

| Strains and binary plasmids | % of explants having: | | |
| --- | --- | --- | --- |
| | GUS+ spots | large GUS+ areas | GUS+ axillary buds or wholly GUS+ shoots |
| GV 2260 (pGUS intron) | 21.5 | 4.5 | 0 |
| C58' 3 (pGA 492-GI) | 0 | 0 | 0 |
| LBA 4404 (pGA 492-GI) | 38.5 | 18.5 | 1 |

Only the regenerated shoots derived from cocultures with GV 2260 (pGUS intron) and LBA 4404 (pGA 492 GI) show expression of glucoronidase (GUS+activity). With the C58'3 strain, no GUS+activity was detected. The percentage of bombarded and cocultured explants showing at least one shoot with large areas expressing a GUS+activity is 4 times higher when the explants are cocultured with the LBA 4404 strain (pGA 492-GI) than when they are cocultured with the GV 2260 strain (pGUS-intron). Only the LBA 4404 strain makes it possible to obtain secondary meristems or shoots having a GUS+activity in all the cells.

EXAMPLE 5

Influence of the bacterial strain and the binary plasmid on the efficiency of genetic transformation of semimeristems The semimeristems are bombarded and cocultured with the strains LBA 4404 (pGA 492-GI), C58'3 (pGA 492-GI) and GV 2260 (p35S GUS intron) which are described in Example 4.

After culturing for 6 weeks according to the procedure described in Example 3, a number of semimeristems capable of developing shoots in the presence of kanamycin (100 mg/l) was recorded (Table 4).

The results are as follows:

The transformation efficiency is defined as the percentage of bombarded and cocultured semimeristems which give at least one kanamycin-resistant shoot.

| Strains and binary plasmids | Transformation efficiency (%) |
| --- | --- |
| C58' 3 (pGA 492-GI) | 0 |
| LBA 4404 (pGA 492-GI) | 4.5 |
| GV 2260 (p35S Gus intron) | 1 |

The coculturing of semimeristems with the LBA 4404 strain (pGA 492-GI) makes it possible to obtain a percentage of 4.5% of semimeristems which initiate transformed shoots resistant to kanamycin after 6 weeks in the M2 medium containing 100 mg/l of kanamycin. This percentage is 4 times greater than the percentage obtained with the GV 2260 strain (p35S Gus intron). With the C58'3 strain, no kanamycin-resistant shoot was obtained.

The LBA 4404 strain (pGA 492-GI) was chosen for the standard procedure (described in FIG. 3) because it makes it possible to routinely obtain a large number of wholly transformed shoots.

EXAMPLE 6

Influence of the concentration of kanamycin on the genetic transformation of semimeristems The semimeristems bombarded and cocultured with the LBA 4404 strain (pGA 492-GI) are cultured for 6 weeks in the presence of various concentrations of kanamycin 50, 100, 200, 400 mg/l in the M2 medium (according to the procedure described in Example 3). After 6 weeks of culture, the green shoots resistant to kanamycin are subjected to a test for the expression of glucuronidase (procedure described in Example 1, part 1.5).

The results are as follows (Table 5):

| Kanamycin concentration | Percentage of semimeristems giving: | | |
| --- | --- | --- | --- |
| | axillary shoots with GUS+ spots | shoots carrying large GUS+ areas | wholly GUS+ axillary shoots |
| 50 mg/l | 30 | 22.5 | 3.3 |
| 100 mg/l | 30.5 | 18.5 | 3.3 |
| 200 mg/l | 29 | 15.5 | 0 |
| 400 mg/l | 24 | 12 | 0.5 |

Table 5 shows the effects of kanamycin on the percentage of semimeristems showing glucuronidase expression. 25 to 30% of the bombarded and cocultured meristems give at least one shoot which expresses glucuronidase in the form of spots regardless of the concentration of kanamycin used. Selection on a high concentration of kanamycin (200 mg/l or 400 mg/l) slightly reduces the percentage of semimeristems giving shoots with GUS+spots but substantially reduces the percentage of semimeristems giving shoots with large GUS areas. Only the concentrations of 50 mg/l and 100 mg/l make it possible to obtain, after selection, 3.3% of wholly transformed shoots. The concentration of 50 mg/l of kanamycin was chosen for the standard procedure (described in FIGS. 3 and 4); at this concentration, resistant shoots expressing glucuronidase can be obtained routinely and in a large number.

EXAMPLE 7

Efficiency of transformation of various sunflower genotypes 7.1—Capacity for vegetative multiplication of semimeristems and for new formation of newly formed leaf meristems.

In a preliminary experiment, 50 sunflower lines were selected for their capacity to induce axillary shoots from semimeristems and newly formed leaf meristems on the leaves of the shoots. All the lines tested regenerate axillary shoots from semimeristems with percentages varying from 20 to 90%. All the lines tested give 7 to 44% of semimeristems which form axillary shoots carrying newly formed leaf meristems at the upper surface of the leaves. More than 60% of the lines tested give at least 20% of semimeristems which regenerate axillary shoots with newly formed leaf meristems on the leaves.

7.2—Capacity for transformation of semimeristems

Among the 50 lines, 10 having the greatest capacity for vegetative multiplication of shoots and the initiation of meristems were chosen in order to evaluate the efficiency of genetic transformation of semimeristems.

About 200 semimeristems for each of the 16 lines were bombarded and cocultured with the LBA 4404 strain (pGA 492-GI), and then cultured on the M2 medium containing 400 mg/l of augmentin and 50 mg/l of kanamycin for 6 weeks (according to the procedure described in Example 3).

After 6 weeks of selection of the shoots resistant to kanamycin (50 mg/l), all the lines tested give at least one semimeristem which form axillary shoots resistant to kanamycin, showing that the method described makes it possible to obtain wholly transformed sunflower plants for 100% of the sunflower lines tested (Table 6).

The transformation efficiency varies from 0.5 to 6% according to the lines. The lines which give the highest transformation efficiencies (LG15, LG60 and LG61) also had the greatest capacity for vegetative multiplication from semimeristems, which suggests a positive correlation between the capacity for transformation by the method described in the invention and the capacity for regeneration from semimeristems.

| Sunflower lines | % of semimeristems giving axillary shoots | % of semimeristems giving shoots with newly formed leaf meristems | Transformation efficiency |
|---|---|---|---|
| HA 300 | 78.5 | 17.5 | 2.5 |
| LG 1 | 65 | 42.5 | 0.5 |
| LG 15 | 85 | 44.5 | 3.4 |
| RHa 356 | 71 | 43.5 | 2 |
| RHa 362 | 46 | 37.5 | 0.5 |
| RHa 274 | 70.5 | 13.5 | 2.6 |
| RHa 297 | 66 | 39.5 | 1.4 |
| RHa 359 | 66 | 39.5 | 2.3 |
| LG 60 | 90 | ND | 3.6 |
| LG 61 | 90 | ND | 6 |

EXAMPLE 8

Analysis of the transformed plants regenerated from semimeristems and their progeny The kanamycin-resistant shoots, which are transferred in the SORBAROD system and acclimatized in a greenhouse (Example 3), are cultured in a greenhouse. On these plants, several branches develop, each with a capitulum.

Analyses of the glucuronidase activity were carried out on each plant and each branch. For each branch, a test of glucuronidase activity was carried out on a leaf, a ligulate flower (flower situated on the periphery of the capitulum having a petal) and on a floret (internal flower of the capitulum without petal). The aim of the analyses of the GUS activity is to determine the percentage of wholly transformed plants which will give a progeny whose inserted genes (NPT II gene and GUS gene) will segregate in a Mendelian fashion. Such plants must be composed of transformed cells in all the tissues and the organs and especially in the floral organs containing the ovules and the pollen which will give, after fertilization, the zygotic embryo contained in the seed. A plant is considered to be wholly transformed when it has a GUS activity in all its branches and for each of the branches, in the leaves, the florets and the ligulate flowers.

Table 7 shows that 92% of the transformed plants cultured in a greenhouse by the technique described in this invention are wholly transformed: for these plants, all the branches have leaves, ligulate flowers and florets expressing a glucuronidase activity.

| T0 plants wholly GUS+ | T0 plants leaves GUS+ flowers GUS− | T0 plants branch GUS+ branch GUS− |
|---|---|---|
| 92% | 6.5% | 1.5% |

On the other hand, 8% of the transformed plants exhibit characteristics of chimeric plants:

1.5% of plants have some branches in the leaves and the capitula show a GUS+ activity and other branches whose leaves and capitula do not show any glucuronidase activity.

These chimeric plants are derived from shoots some of whose axillary buds were transformed and other axillary buds were not transformed.

6.5% of plants have branches whose leaves have a glucuronidase activity and whose florets or ligulate flowers do not exprime glucuronidase.

These chimeric plants are derived from shoots including the axillary buds composed of transformed cells in the vegetative meristematic ring at the origin of the vegetative parts (leaves, stems and petioles) and non-transformed cells in the medullary part of the meristem at the origin of the floral and reproductive organs.

The percentage of chimeric plants obtained is low (8%). In the technique described in the present invention, the plants having a ligulate flower or a floret not expressing glucuronidase activity are considered to be chimeric and are eliminated.

The wholly transformed plants are self-fertilized by several successive passages in order to spread the pollen on each capitulum. The seeds are then harvested on the two months after the fertilization. The seeds are treated by steeping for 5 hours in ethrel (0.1% solution in water), and then decorticated and sterilized (according to the procedure described in Example 1). The sterile seeds are then allowed to germinate in the M0 medium containing 100 mg/l of kanamycin in Phytatray culture dishes (SIGMA Ref. P1552). After 15 days of germination, the kanamycin-resistant transformed plantlets are green and develop green leaves. The kanamycin-sensitive non-transformed plantlets are white and do not develop any root or green leaf.

A test of glucuronidase activity is carried out on the green leaves of kanamycin-resistant plantlets.

The percentage of kanamycin-resistant plantlets and the percentage of plants expressing the GUS gene are determined (Table 8).

| T1 lines | Number of seeds sown | % of seeds resistant to kanamycin | % of GUS+ seeds |
| --- | --- | --- | --- |
| 80-2 | 37 | 78 | 76 |
| 84-1-2 | 40 | 72 | ND |
| 79-1 | 51 | 74 | 20 |
| 107-1 | 8 | 38 | 38 |
| 139-6 | 14 | 35 | 35 |
| 80-1 | 34 | 71 | 71 |
| NT | 40 | 0 | 0 |

The segregations of the GUS and NPT II genes in the progenies of the wholly transformed plants follow a mendelian-type segregation because, in practically all cases, at least ¾ of the plants express the NPT II gene or the GUS gene and ¼ of plants are non-transformed. These results confirm that the plants produced are indeed wholly transformed and are not chimeric.

Molecular analyses of these transgenic plants were carried out in order to identify the number of insertion loci, the copy number of TDNA and in order to map the borders of the insert.

What is claimed is:

1. A method for producing a transgenic sunflower, said method comprising:

a) genetically transforming a meristematic explant from said sunflower;

b) culturing said transformed meristematic explant on a selection medium;

c) detecting among axillary buds and/or newly formed leaf buds, the buds which are transformed;

d) removing said transformed buds detected in step c) from the cultured transformed meristematic explant;

e) culturing said transformed buds removed in step d) on a selection medium;

f) repeating steps c), d) and e) at least three times; and, g) regenerating said cultured transformed buds to obtain a transgenic sunflower, wherein at least 92% of transgenic sunflowers are wholly transformed in the $T_0$ generation.

2. The method according to claim 1, wherein the meristematic explant is precultured for 5 to 30 days in a culture medium comprising a cytokine prior to being transformed.

3. The method according to claim 1, wherein the transformation step a) comprises the steps of:

a) bombarding at least part of the meristematic explant with microparticles; and b) contacting said bombarded explant with Agrobacterium, wherein said Agrobacterium comprises at least one nucleic acid sequence which is introduced into meristematic cells.

4. The method according to claim 3, wherein the nucleic acid sequence introduced into the meristematic cells further comprises a nucleic acid sequence encoding an agent that confers resistance to an antibiotic.

5. The method according to claim 3, wherein said Agrobacterium is *Agrobacterium tumefaciens* containing a binary vector.

6. The method according to claim 1, wherein the transformation step a) comprises the step of: bombarding at least part of the meristematic explant with microparticles that are coated with DNA which are introduced into the meristematic cells.

7. The method according to claim 6, wherein the transformation step a) further comprises the step of contacting the meristematic explant with a suspension of Agrobacterium.

8. The method according to claim 1, wherein said selection medium or said culture medium is a Murashige Skoog medium supplemented with about 0.05 to 2.0 mg/l 6-benzylaminopurine and wherein said selection medium further comprises at least one selective agent.

9. The method according to claim 8, wherein said selective medium further comprises bacteriostatic agents.

10. The method according to claim 8, wherein said Murashige Skoog medium is supplemented with 0.1 mg/l 6-benzylaminopurine.

11. The method according to claim 8, wherein said selective agent is kanamycin.

12. The method according to claim 8, wherein said selective medium or said culture medium is supplemented with a phenolic compound that activates the Agrobacterium vir genes.

13. The method according to claim 12, wherein the phenolic compound is acetosyringone.

14. The method according to claim 1, wherein the sunflower is *Helianthus annuus*.

* * * * *